United States Patent
Ark et al.

(10) Patent No.: US 9,504,497 B2
(45) Date of Patent: Nov. 29, 2016

(54) ILIOSACRAL POLYAXIAL SCREW

(71) Applicant: K2M Inc., Leesburg, VA (US)

(72) Inventors: Timmon Ark, Falls Church, VA (US);
Daniel Genovese, Arlington, VA (US);
Theo Choi, Arlington, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/270,530

(22) Filed: May 6, 2014

(65) Prior Publication Data

US 2014/0243900 A1    Aug. 28, 2014

Related U.S. Application Data

(63) Continuation of application No. 13/771,140, filed on Feb. 20, 2013, now Pat. No. 8,979,898.

(51) Int. Cl.
*A61B 17/70*    (2006.01)

(52) U.S. Cl.
CPC ....... *A61B 17/7037* (2013.01); *A61B 17/7032* (2013.01); *A61B 17/7055* (2013.01); *Y10T 29/49826* (2015.01)

(58) Field of Classification Search
CPC .......... A61B 17/7001; A61B 17/7002; A61B 17/7032; A61B 17/7034; A61B 17/7035; A61B 17/7037; A61B 17/7038
USPC .......... 606/246, 264–279, 300–321
See application file for complete search history.

(56) References Cited

U.S. PATENT DOCUMENTS

| | | | |
|---|---|---|---|
| 5,360,431 A | 11/1994 | Puno et al. | |
| 5,443,467 A * | 8/1995 | Biedermann | A61B 17/7032 606/308 |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,549,608 A | 8/1996 | Errico et al. | |
| 5,554,157 A | 9/1996 | Errico et al. | |
| 5,584,834 A | 12/1996 | Errico et al. | |
| 5,586,984 A | 12/1996 | Errico et al. | |
| 5,647,873 A | 7/1997 | Errico et al. | |
| 5,669,911 A | 9/1997 | Errico et al. | |
| 5,672,176 A | 9/1997 | Biedermann et al. | |
| 5,690,630 A | 11/1997 | Errico et al. | |
| 5,733,285 A | 3/1998 | Errico et al. | |

(Continued)

FOREIGN PATENT DOCUMENTS

GB    2483531 A    3/2012

OTHER PUBLICATIONS

European Search Report, Application No. EP 14 15 5355 dated May 15, 2014.

(Continued)

*Primary Examiner* — Ellen C Hammond
*Assistant Examiner* — Christina Negrellirodrigue
(74) *Attorney, Agent, or Firm* — Carter, DeLuca, Farrell & Schmidt, LLP

(57) ABSTRACT

Provided is an iliosacral polyaxial screw system. A multiple part insert member is provided to secure the screw to the housing of the assembly to accommodate screws in which the shank diameter of the screw is greater than the bottom opening of the screw housing or greater than the opening of a ring member designed to capture the head of the screw in the housing.

6 Claims, 11 Drawing Sheets

(56) References Cited

U.S. PATENT DOCUMENTS

| | | |
|---|---|---|
| 5,733,286 A | 3/1998 | Errico et al. |
| 5,797,911 A | 8/1998 | Sherman et al. |
| 5,817,094 A | 10/1998 | Errico et al. |
| 5,863,293 A | 1/1999 | Richelsoph |
| 5,885,286 A | 3/1999 | Sherman et al. |
| 5,964,760 A | 10/1999 | Richelsoph |
| 6,074,393 A | 6/2000 | Sitoto |
| 6,090,110 A | 7/2000 | Metz-Stavenhagen |
| 6,261,287 B1 | 7/2001 | Metz-Stavenhagen |
| 6,273,888 B1 | 8/2001 | Justis |
| 6,280,442 B1 | 8/2001 | Barker et al. |
| 6,355,040 B1 | 3/2002 | Richelsoph et al. |
| RE37,665 E | 4/2002 | Ralph et al. |
| 6,402,752 B2 | 6/2002 | Schäffler-Wachter et al. |
| 6,485,491 B1 | 11/2002 | Farris et al. |
| 6,537,276 B2 | 3/2003 | Metz-Stavenhagen |
| 6,565,569 B1 | 5/2003 | Assaker et al. |
| 6,869,433 B2 | 3/2005 | Glascott |
| 6,872,209 B2 | 3/2005 | Morrison |
| 6,875,211 B2 | 4/2005 | Nichols et al. |
| 6,881,215 B2 | 4/2005 | Assaker et al. |
| RE39,089 E | 5/2006 | Ralph et al. |
| 7,128,743 B2 | 10/2006 | Metz-Stavenhagen |
| 7,144,396 B2 | 12/2006 | Shluzas |
| 7,211,086 B2 | 5/2007 | Biedermann et al. |
| 7,223,268 B2 | 5/2007 | Biedermann |
| 7,695,497 B2 | 4/2010 | Cordaro et al. |
| 8,133,262 B2* | 3/2012 | Whipple ...................... 606/269 |
| 2004/0097933 A1* | 5/2004 | Lourdel et al. ................. 606/61 |
| 2005/0203516 A1 | 9/2005 | Biedermann et al. |
| 2005/0277928 A1 | 12/2005 | Boschert |
| 2006/0241769 A1 | 10/2006 | Gordon et al. |
| 2006/0247631 A1 | 11/2006 | Ahn et al. |
| 2008/0004625 A1* | 1/2008 | Runco ................ A61B 17/7037 606/273 |
| 2008/0015579 A1 | 1/2008 | Whipple |
| 2008/0161853 A1 | 7/2008 | Arnold et al. |
| 2009/0105716 A1 | 4/2009 | Barrus |
| 2009/0105769 A1 | 4/2009 | Rock et al. |
| 2009/0149887 A1 | 6/2009 | Schlaepfer et al. |
| 2009/0163956 A1 | 6/2009 | Biedermann et al. |
| 2009/0163962 A1 | 6/2009 | Dauster et al. |
| 2009/0182384 A1 | 7/2009 | Wilcox et al. |
| 2010/0179692 A1 | 7/2010 | Lu et al. |
| 2011/0093021 A1 | 4/2011 | Fanger et al. |
| 2011/0276095 A1 | 11/2011 | Bar et al. |
| 2012/0303063 A1* | 11/2012 | Cahill ................ A61B 17/7032 606/270 |
| 2013/0012003 A1 | 1/2013 | Haukka et al. |

OTHER PUBLICATIONS

European Examination Report dated Jun. 1, 2015, issued in European Application No. 14 155 355.

European Office Action dated Dec. 23, 2015, issued in EP 14 155 355.2.

European Office Action dated Jul. 8, 2016 in corresponding EP Application No. 14155355.2-1501.

* cited by examiner

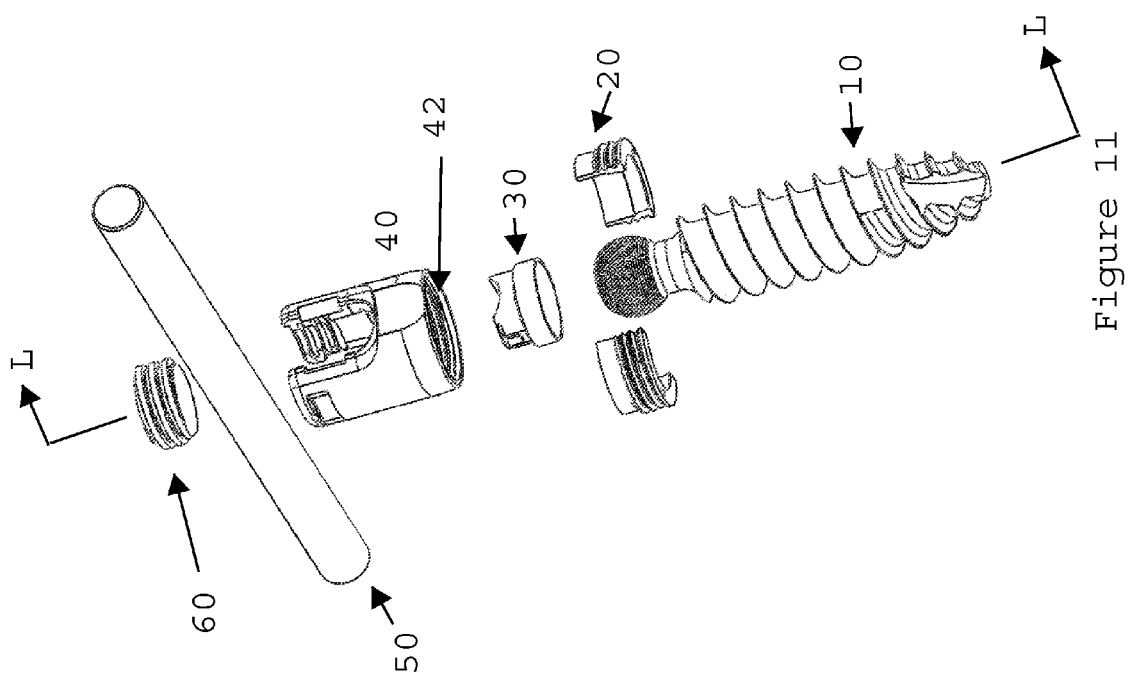

ILIOSACRAL POLYAXIAL SCREW

CROSS REFERENCE TO RELATED APPLICATIONS

This application is a Continuation Application of U.S. patent application Ser. No. 13/771,140 filed on Feb. 20, 2013, which is expressly incorporated herein by reference in its entirety.

BACKGROUND

1. Technical Field

The present disclosure relates to polyaxial screws and, more particularly, to an iliosacral polyaxial screw assembly.

2. Background Art

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include, PEEK interbody spacers, metal cages and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. The opposing pair of longitudinally linked rods is commonly disposed along the long axis of the spine via a posterior approach. Pedicle screws can be manufactured from any biocompatible material, including cobalt chrome, stainless steel, titanium and PEEK (polyetheretherketone).

To meet the problem of providing a rigid screw and rod construct, especially for addressing the demands of iliosacral constructs, larger rod and screw constructs have been made to improve the strength of the screw and rod construct. Spinal screws are typically made of titanium alloy. However, when large deformity corrections are necessary these screws are not always strong enough. Larger diameter titanium screws have been made for these applications, but a larger screw requires a unique design and/or assembly of the polyaxial screw to allow for a larger shank portion of the screw while still maintaining the same screw head size that mates with the housing of the screw.

Therefore, a need exists for a cost effective, rigid screw and rod construct that can still maintain large, stiff deformity corrections that impact the iliosacral junction.

SUMMARY OF THE DISCLOSURE

The present disclosure is directed to a polyaxial screw including a housing, a bone screw member, a wedge member and an insert. The bone screw member is selectively positionable at a plurality of angles relative to the housing when engaged to the housing and securable relative to the housing at a cone angle of up to approximately 80 degrees. The bone screw member includes a head and a threaded shaft extending from the head. The head is selectively securable within the housing by use of the insert member. The head may include surface texture that frictionally engages with the wedge member such that a user applied force is necessary to reposition the bone screw member relative to the wedge member when the bone screw member is disposed in engagement with the wedge member. The wedge member is positionable within the housing adjacent to the head of the bone screw member when the wedge member and the head of the bone screw member are positioned within the housing. A set screw is positionable within the housing to secure a rod member within the housing adjacent the wedge member.

The wedge member may contain one or more grooves in an outer surface of the wedge member. The groove defines one or more flaps. The one or more flaps are flexibly attached to the wedge member to enable the wedge member to flex an amount sufficient to maintain the head of the bone screw member in constant frictional contact with the wedge member when the bone screw member is moved relative to the wedge member.

The wedge member may define a cavity having a surface with a plurality of radii of curvature to accommodate rod members of variously sized diameters. The surface of the cavity may define a first section with a first radius of curvature, a second section with a second radius of curvature, and a third section with a third radius of curvature. In this respect, the plurality of radii of curvature defines a compound curve that provides two or more lines of contact on a plurality of different diameter rod members.

The outer surface of the wedge member may have a non-round shape to prevent mis-orientation of the wedge member when positioning the rod member adjacent the wedge member. The wedge member may include a protuberance on the outer surface of the wedge member and the housing may define a slot on an inner surface of the housing. The protuberance and the slot may be engagable to maintain the alignment of the wedge member with respect to the housing.

An insert member may be securable to the housing to prevent the bone screw member from disassembling from the housing. The housing may include a collar extending therefrom. The collar may define a cut out to facilitate the positioning of the head within the housing. The insert member may be comprised of at least two pieces and is securable (such as by friction fit, gluing, threads, welding or the like, or combinations thereof) to the housing to cover part of the through hole of the housing after the head of the bone screw member is positioned within the housing.

An insert member receives a bone screw such that a neck of the screw shaft and/or the screw head resides in the through hole of the insert member. The through hole is small enough to not allow the screw head to fall through it and thus captures the screw head within the housing and secures the screw to the housing. The insert may have threads or other such attachment means to be securable to the housing to prevent the housing-bone screw member assembly from coming apart. The insert member may be comprised of two or more pieces so that all or some of the bone screw shank portion and the screw head portion can be larger than the through hole of the insert member. In some instances a large shank diameter screw may be needed depending upon the size of the patient's anatomy and depending upon the location for placement of the screw. Therefore, if the insert is made of two pieces the insert halves can be placed around the head and/or neck portions of the bone screw and threaded into the housing as a subassembly, then the screw shaft does not need to pass through either the housing through hole (in a top loading configuration) or a ring member through hole (in a bottom loading configuration) to assemble the bone screw member with the insert. The bone screw member is selectively positionable at a plurality of angles relative to the housing when engaged to the housing and securable relative to the housing at a cone angle of up to approximately 80 degrees. The bone screw member has a threaded shaft and a head. The bone screw member has a head supported within the housing and a shaft that extends from the housing. The shaft defines a longitudinal axis between leading and trailing ends of the shaft. The shaft is selectively movable relative to the housing and may include a buttress thread form with a pressure flank portion that is nearly perpendicular to the longitudinal axis of the shaft to maximize load resistance of the pressure flank portion. The leading end of shaft may be tapered such that the buttress thread form tapers along a length of the tapered leading end. The length of the tapered leading end of the shaft may be approximately ⅓ of a length of the shaft. The pressure flank portion of the buttress thread form may be positioned at an angle offset from a perpendicular orientation relative to the longitudinal axis of the shaft by an amount ranging between approximately 1 and 5 degrees. The angle may be greater than 90 degrees. The buttress thread form of the shaft may be a double lead thread. Such thread configuration is disclosed in U.S. patent application Ser. No. 13/595,533, which is hereby incorporated by reference in its entirety.

According to one aspect, a polyaxial screw includes a bone screw member and a housing. The bone screw member includes a head having a threaded shaft extending from the head. The housing is positionable on the head of the bone screw and has a distal opening. The bone screw member is positionable at a plurality of angles relative to the housing when engaged to the housing and securable relative to the housing at angles within a cone angle of up to approximately 80 degrees. A set screw is positionable within the housing to secure a rod member within the housing adjacent the wedge member.

According to yet another aspect, the present disclosure is directed to a method of assembling a polyaxial screw. The method includes providing a polyaxial screw including a bone screw member and a housing. A wedge member is inserted into the bottom of the housing until seated against structure of the housing configured to limit travel of the wedge member toward the top of the housing. The bone screw member includes a head having a threaded shaft extending from the head and an unthreaded neck portion defined between the head and the threaded shaft. An insert member which consists of two halves is placed around the head and/or neck of the screw and inserted into the housing with the screw head until the head is adjacent the wedge member. The insert portions and housing may be welded together at the bottom, distal edge to prevent disassembly. Alternatively or in addition, threads on the exterior of the insert halves may engage threads on the interior, bottom portion of the housing. A spinal rod is placed into the U shaped channel of the housing and into the recess of the wedge member and a set screw is threaded into the top portion of the housing such that the set screw pushes the rod onto the wedge member which is then pushed into contact with the screw head, which in turn is pressed against the insert member halves secured to the housing, thus locking the screw into place.

BRIEF DESCRIPTION OF THE DRAWINGS

The foregoing and other features of the iliosacral polyaxial screw system will become apparent to one skilled in the art to which the disclosed system and devices relate upon consideration of the following description of exemplary embodiments with reference to the accompanying drawings, wherein:

FIG. 11 shows an exploded bottom perspective view of the embodiment of FIG. 1.

DETAILED DESCRIPTION OF PREFERRED EMBODIMENTS

Figure 1:
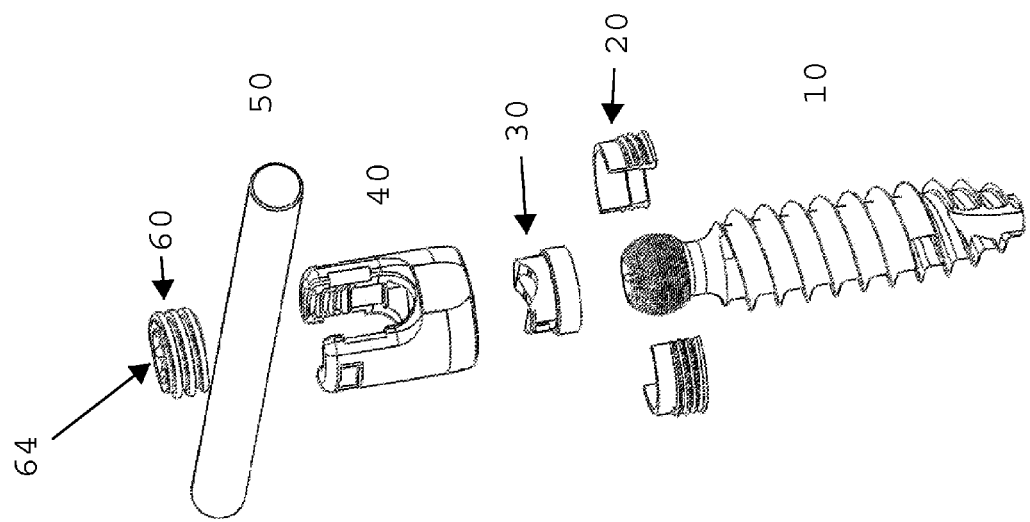
FIG. 1 shows an exploded view of one embodiment.

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed. Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" or "cranial" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Referring now to the drawings, the spinal implant of one embodiment includes a bone screw having a threaded shank 10, a head 12 and a neck 14 between the head and the threaded shank. The implant further includes a housing 40 having an open through bore 44, a wedge member 30 configured to be seated in the through bore 44, and at least two insert members configured to surround the screw neck and/or head. The insert members together define a complete ring around the screw head and/or neck and engage the housing at the bottom opening to secure the head within the housing with the top of the head adjacent the bottom of the wedge member. The housing further includes a slot to receive a spinal rod 50, with threaded segments on the interior walls of the of the upright arm segments that define the rod-receiving slot, and a threaded set screw 60 configured to engage the threaded segments of the upright slot-defining walls to secure the rod to the set screw assembly and drive the rod to exert force onto the wedge member and screw head against the insert members which are fixed relative to the housing, to lock the screw in position relative to the housing.

Figure 2:
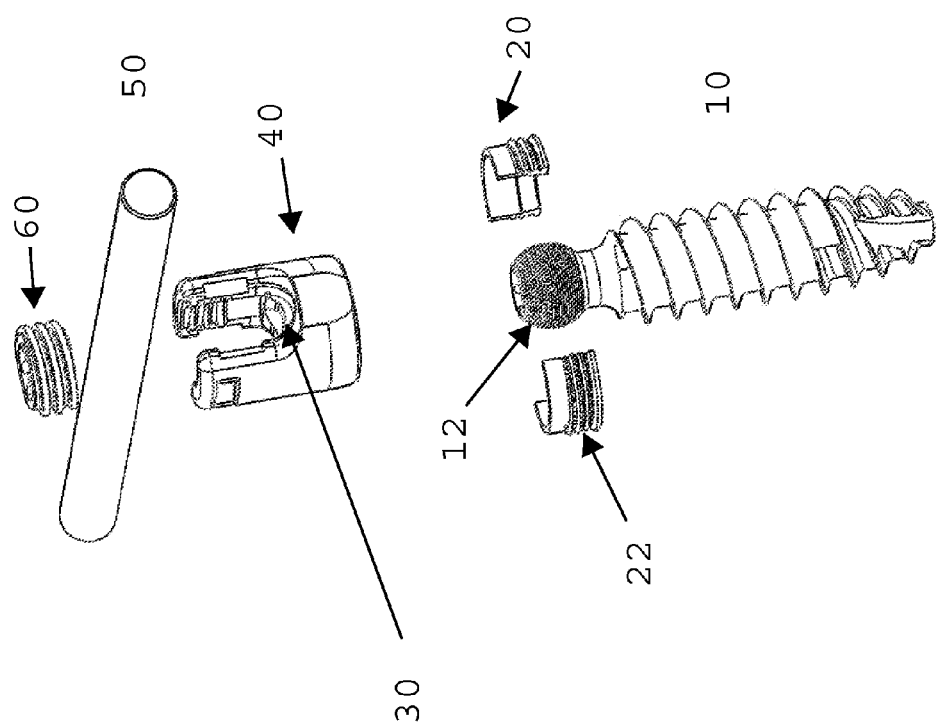
FIG. 2 shows an assembly view of the embodiment of FIG. 1 with the wedge member inserted into the housing and seated in place.
Figure 3:
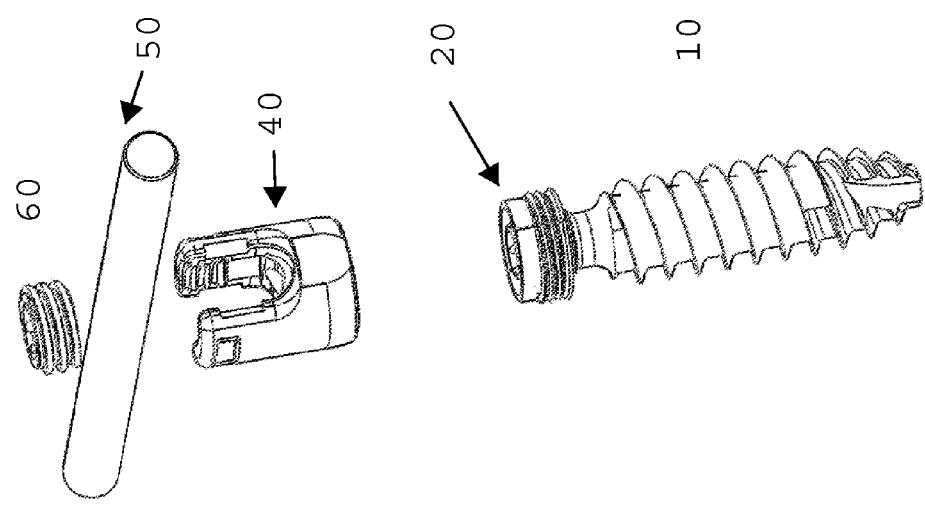
FIG. 3 shows an assembly view of the embodiment of FIG. 1 with the wedge member inserted into the housing and the insert portions surrounding the screw head.
Figure 4:
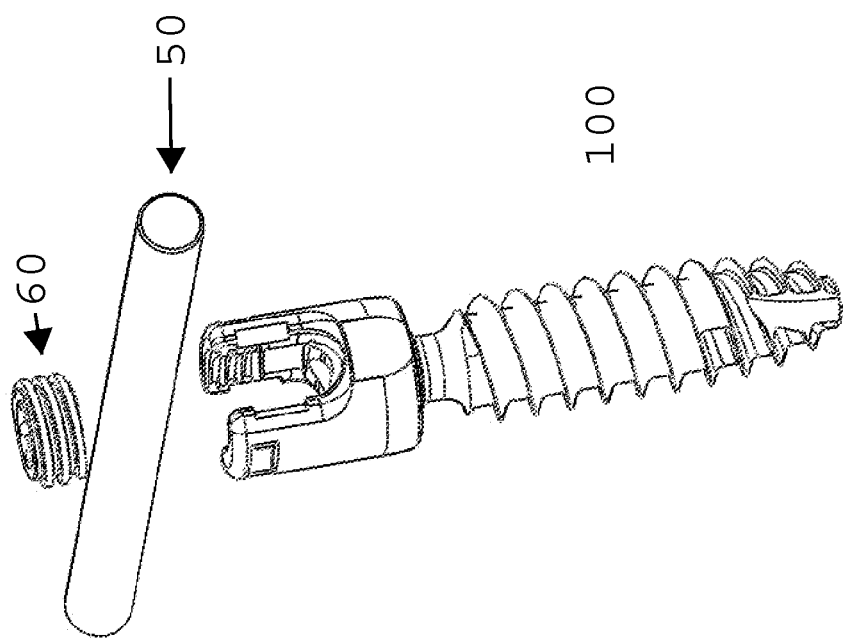
FIG. 4 shows an assembly view of the embodiment of FIG. 1 with the screw insert sub-assembly inserted into the housing.
Figure 5:
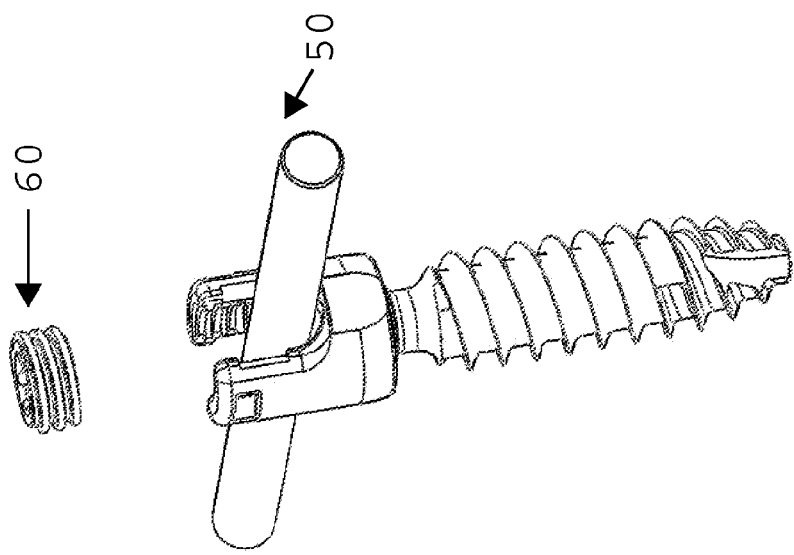
FIG. 5 shows an assembly view of the embodiment of FIG. 1 with the rod installed in the housing of the screw assembly.
Figure 6:
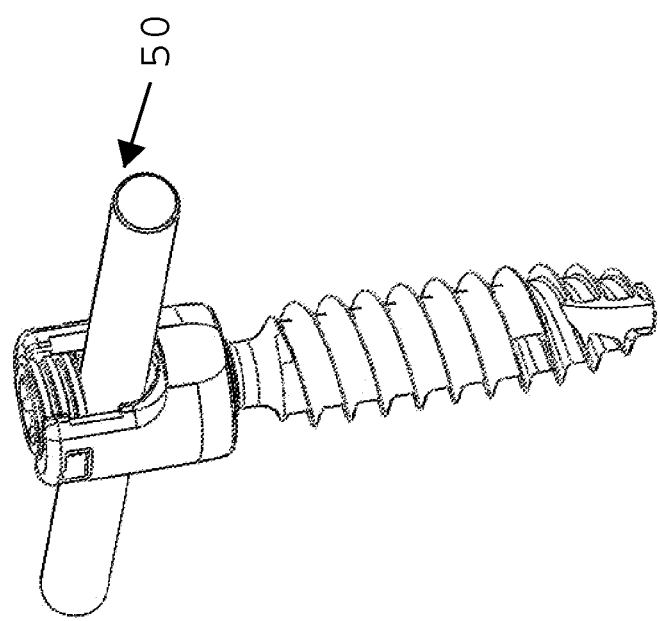
FIG. 6 shows an assembly view of the embodiment of FIG. 1 with the set screw installed with the screw assembly.
Figure 8:
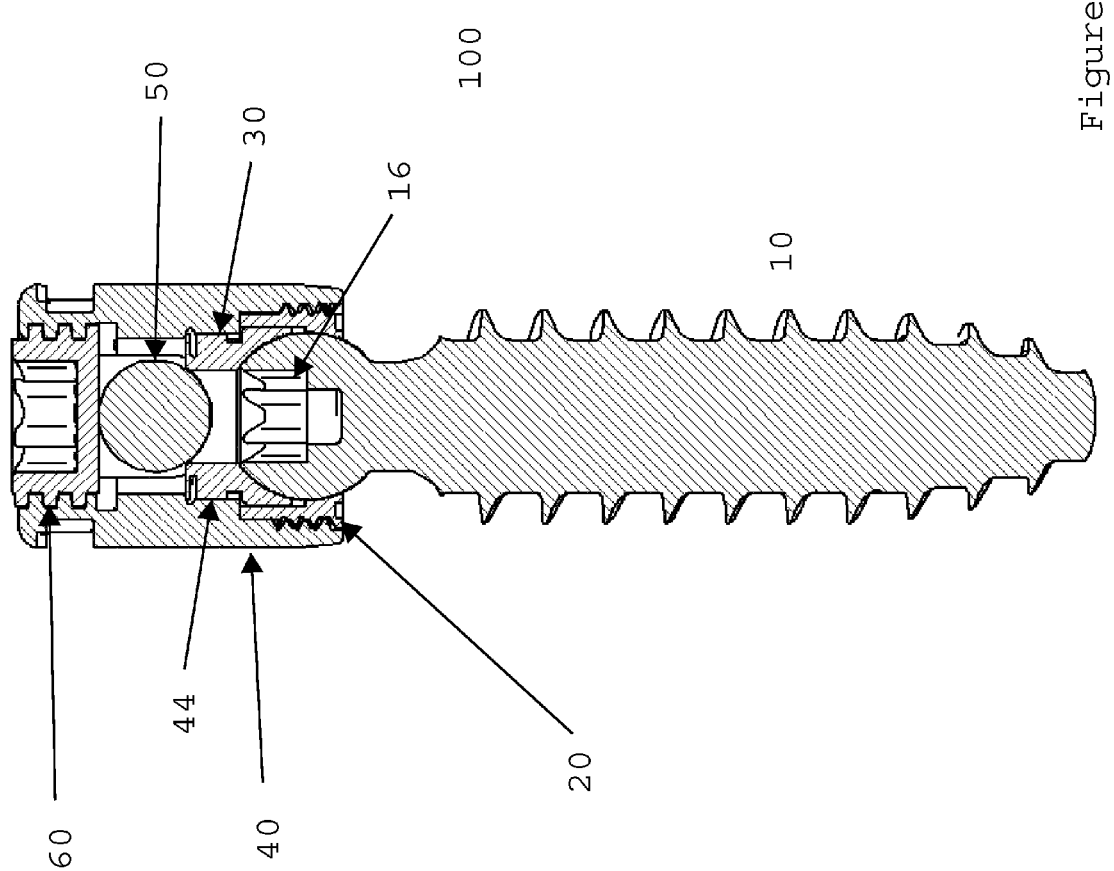
FIG. 8 shows a section view of the embodiment of FIG. 1.
Figure 9:
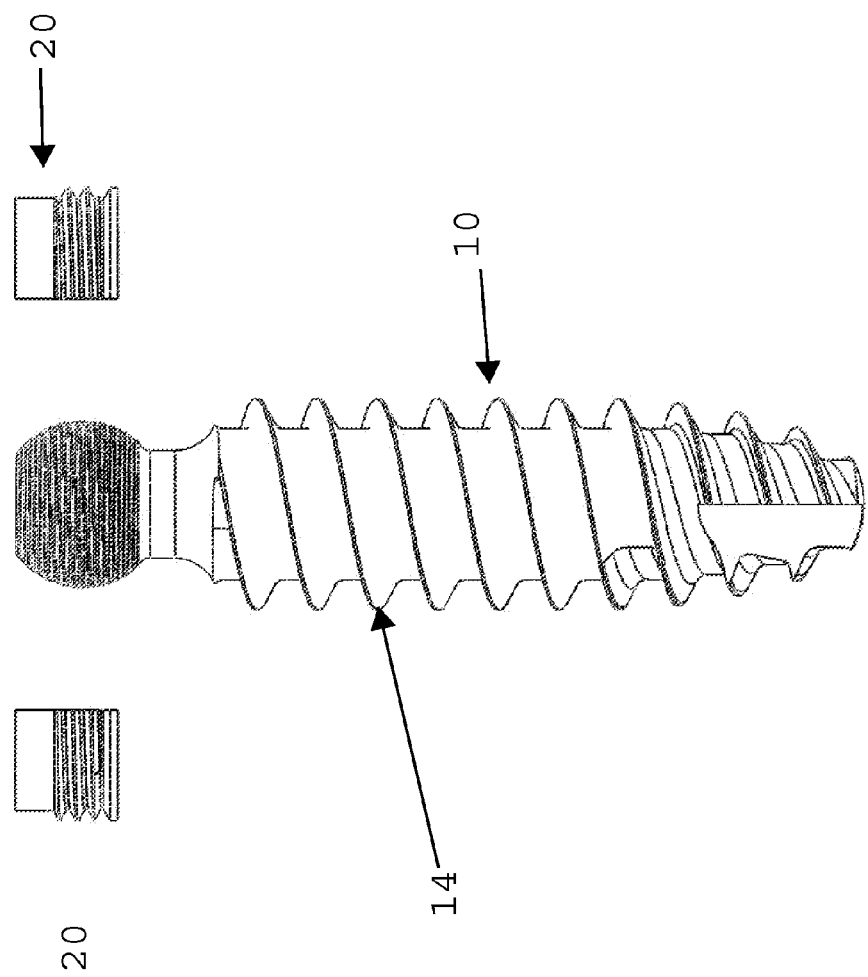
FIG. 9 shows a side view of the screw shank and insert portions of one embodiment.
Figure 10:
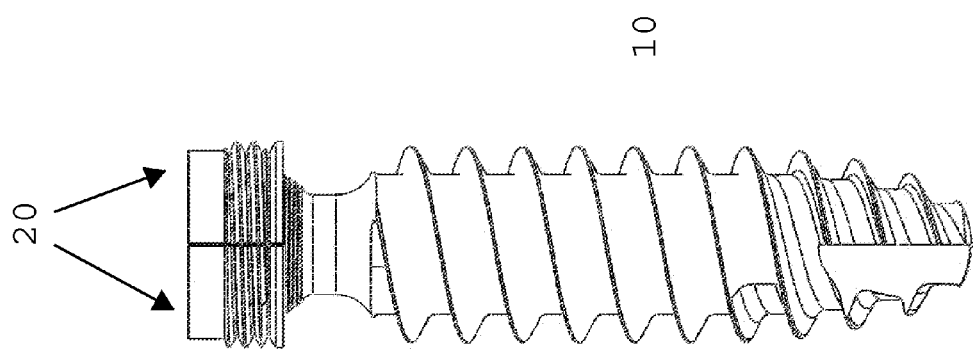
FIG. 10 shows a sub-assembly of the insert portions of one embodiment surrounding the screw head.

In one embodiment the wedge member 30 is inserted into the through hole 44 of the housing 40 from the distal, bottom end of the housing 40 (see FIGS. 2 and 8) until the wedge member becomes seated in the housing and cannot travel further toward the proximal or top end of the housing due to features in the housing that creates a narrowed portion of the through hole 44 through which the wedge member cannot pass. When the wedge member is seated in the housing, recess 32 which is configured to receive rod 50 protrudes above the bottom of slot 30 (see FIGS. 2-3) so a rod 50 inserted into the slot will seat in recess 32. The insert portions 20 are placed around the head 12 of the screw 10 to encircle the head as indicated in FIGS. 3 and 10. The screw and insert sub-assembly is inserted into the distal end of the housing 40 and threaded into place using the external threads 22 of the insert portions 20 and the internal bottom threads 42 of the housing 40, as indicated in FIGS. 3, 4 and 8. Optionally, the distal edge of the housing 40 and insert portions 20 may be welded or glued together to prevent disassembly. Once the screw assembly 100 is inserted into the body by driving the screw into bone so that the screw shaft threads engage the bone, a spinal rod 50 can be placed lengthwise in the slot and into recess 32 of the wedge member 30, as indicated in FIG. 5. A set screw 60 may then be inserted into the proximal end of the housing 40 by use of the threads 46 of the housing and the threads 62 of the set screw 60, as indicated in FIGS. 6 and 8 until set screw 60 contacts the top of rod 50 and exerts compressive force onto the rod 50, forcing the rod into the recess 32 of the wedge member 30. The compressive force on wedge member 30 in turn pushes against the screw head 12 and locks the screw assembly 100 into place so that the screw is secured relative to the housing and cannot articulate relative to the housing. It will be understood that in use the screw rod assembly described herein is used as part of multiple screw construct wherein multiple screws are mounted in bone (such as in multiple vertebrae or pedicles) and spinal rod 50 is received in and secured to the housings of the multiple screws to create a screw rod construct.

The bone screw member 10 includes a head 12 and a threaded shaft 14 extending from the head 12. The bone screw member 10 may be a self-starting fastener or self-tapping fastener. The head 12, as best illustrated in FIG. 8, includes a driving recess 16, which may be hexolobular or any other suitable configuration, defined in a proximal surface of the head 12. The driving recess 16 is engagable with any suitable driving instrument (not shown) to enable the driving instrument to advance the bone screw member 10 within bone.

Figure 7:
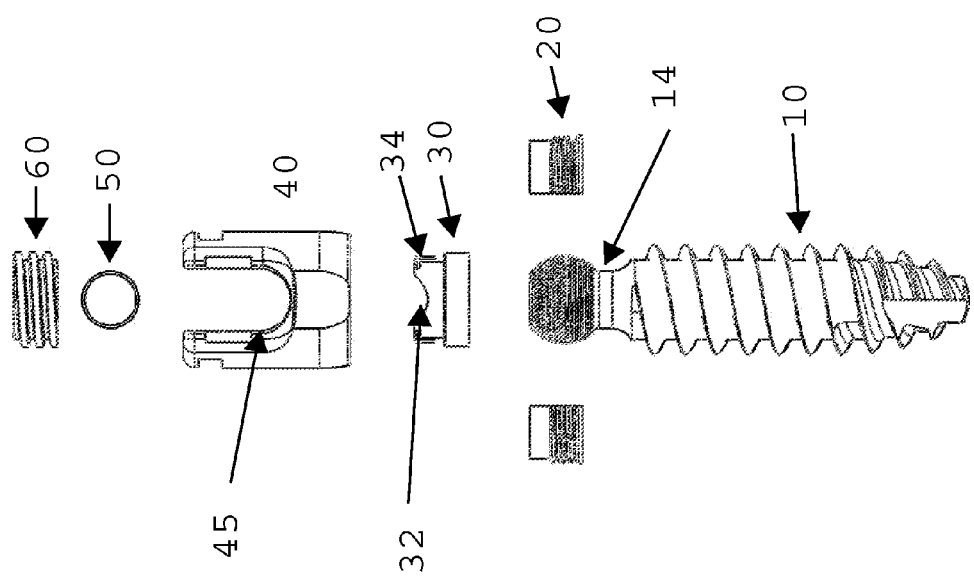
FIG. 7 shows an exploded side view of the embodiment of FIG. 1.

As depicted in FIGS. 7-8, the wedge member 30 is positionable within the housing 40 adjacent the head 12 of the bone screw member 10 when the wedge member 30 and the head 12 of the bone screw member 10 are positioned within the housing 40. Lateral slots 34 adjacent the top of wedge member 30 provide flexible relief tabs to frictionally hold the position of the housing 40 relative to the screw during handling prior to securing of the implant with set screw 60. More particularly, assembly of the screw and screw inserts into the housing exerts a degree of pressure from the upper screw head into the wedge member, thereby flexing the relief tabs to create friction between the screw and the housing to hold the relative position of the screw relative to the housing during handling and insertion of the screw into bone. The screw may be manipulated to overcome the friction, but will not flop around inconveniently during handling. Of course, once the set screw is placed into the housing and exerts force on the rod, the screw becomes fixed relative to the housing. With brief reference to FIG. 6, the set screw 60 is positionable within the housing 40, e.g., via threading engagement 46, 62, to secure the rod member 50 within the housing 40 adjacent the wedge member 30. As can be appreciated, the set screw 60 may be formed of titanium or titanium alloy. The set screw 60 includes a driving interface 64 that is engagable with any suitable driving instrument to threadably engage the set screw 60 within the housing 40.

The wedge member 30 has a curved recess 32, which contains a plurality of radii whose curvature can accommodate variously sized rod members 50. When the rod member 50 is placed against the curved recess 32 of the wedge member 30, the rod member 50 nests easily against the wedge member 30 because the rod member 50 closely corresponds to the arc of the arcuate surfaces of the recess 32. Different diameter rods seat in the corresponding radius of curvature of curved recess 32 to self-center the rod on the wedge member.

As assembled, the bone screw member 100 is fastenable to a bone structure (e.g. vertebra) and the housing 40 is repositionable in a plurality of directions with respect to the bone screw member 100. To this end, the housing 40 is rotatable about the longitudinal axis "L" (see FIG. 11) extending through the polyaxial screw 100 as well as pivotable relative to the longitudinal axis "L". A rod member 50, e.g., a spinal rod, is positionable in the U-shaped channel 45 of the housing 40 and is nested against the arcuate recess of the wedge member 30 as discussed above. The rod member 50 is then secured to the polyaxial screw 100 using a set screw 60. To be more specific, the set screw 60 is inserted into a proximal side of U shaped channel 45 of the housing 40 such that a distal end of the set screw 60 contacts the surface of the rod member 50 and drives the rod member 50 and the wedge member 30 towards the head 12 of the bone screw member 10. Once the desired angular position of the housing 40 is reached, the set screw 60 is tightened further, which compresses the rod member 50, the wedge member 30, and the head 12 of the bone screw member 10 within the housing 40. The frictional engagement between the head 12 of the bone screw member 10 and the bottom portion of the wedge member 30 fixes the angular relationship between the housing 40 and the bone screw member 10.

Additionally, any embodiments of the bone screw members of the presently disclosed polyaxial screws may be provided in any suitable diameter size and/or length. Some of the bone screw members may have diameters of approximately 4.5, 5.5, 6.5, 7.5, 8.5, 9.5, 10.5, 11.5, 12.5 and 13.5 mm and may have lengths of approximately 25-140 mm.

The embodiments described above are illustrative only. It is within the concept of the present invention to include modifications and varying configurations without departing from the scope of the invention that is limited only by the claims included herewith. By way of example only, the wedge member may be provided as a plurality of pieces which when positioned within housing 40 defines the shape of the wedge member shown in the drawings.

In use, the screw assembly 100 may be inserted into the sacrum or iliac crest region of the spine to provide support to a spinal construct. In this region of the spine it is often beneficial to utilize a larger shank screw in these regions of the spine to provide a secure anchor point for the spinal construct.

What is claimed is:

1. A spinal implant comprising:
   a screw having a screw head and a shank portion extending from the screw head, the screw shank portion configured to engage bone;
   a housing having an opening configured to receive the screw head, a distal end of the housing having a threaded inner surface;
   a plurality of threaded insert members configured to surround the screw head and engage the threaded inner surface of the housing to secure the screw head within the housing, the plurality of threaded insert members including a first threaded insert member and a second threaded insert member completely disconnected from the first threaded insert member; and
   a wedge member, wherein the housing receives the wedge member.

2. The spinal implant of claim 1, wherein the wedge member includes a cylindrical wall having a recess configured to receive a spinal rod.

3. The spinal implant of claim 2, wherein the recess of the wedge member includes a plurality of radii of curvature.

4. The spinal implant of claim 1 further comprising a threaded set screw, wherein the housing receives the threaded set screw at its proximal end.

5. The spinal implant of claim 4, wherein the threaded set screw threadably engages an inner surface at the proximal end of the housing to secure a spinal rod adjacent the wedge member.

6. The spinal implant of claim 1, wherein the wedge member includes at least one lateral slot configured to hold a position of the housing relative to the screw.

* * * * *